United States Patent
Zhang

(10) Patent No.: US 10,383,538 B2
(45) Date of Patent: Aug. 20, 2019

(54) CATHETER FOR USE IN RECORDING HIS ELECTROGRAM ALTERNANS AND APPLICATION TO VARIOUS CONDITIONS

(71) Applicant: NEW YORK INSTITUTE OF TECHNOLOGY, Old Westbury, NY (US)

(72) Inventor: Youhua Zhang, Old Westbury, NY (US)

(73) Assignee: NEW YORK INSTITUTE OF TECHNOLOGY, Old Westbur, NY (US)

( * ) Notice: Subject to any disclaimer, the term of this patent is extended or adjusted under 35 U.S.C. 154(b) by 907 days.

(21) Appl. No.: 14/848,901

(22) Filed: Sep. 9, 2015

(65) Prior Publication Data

US 2016/0270684 A1 Sep. 22, 2016

Related U.S. Application Data

(60) Provisional application No. 62/056,902, filed on Sep. 29, 2014.

(51) Int. Cl.
*A61B 5/042* (2006.01)
*A61B 5/00* (2006.01)

(52) U.S. Cl.
CPC .......... *A61B 5/0422* (2013.01); *A61B 5/6852* (2013.01); *A61B 5/6869* (2013.01); *A61B 2562/046* (2013.01)

(58) Field of Classification Search
CPC ... A61B 5/0422; A61B 5/1892; A61B 5/0488; A61B 5/0402; A61B 5/0408; A61B 5/04085; A61B 5/042; A61B 5/0456; A61B 5/046; A61B 5/0464; A61B 5/0472; A61B 5/6846; A61B 5/6852; A61B 5/6855; A61B 5/6869; A61N 1/0476; A61N 2001/0585; A61N 2001/0587
See application file for complete search history.

(56) References Cited

U.S. PATENT DOCUMENTS

| | | | | |
|---|---|---|---|---|
| 5,450,846 | A * | 9/1995 | Goldreyer | A61B 5/0422 600/374 |
| 2002/0161306 | A1* | 10/2002 | Govari | A61B 5/0422 600/509 |
| 2003/0009095 | A1* | 1/2003 | Skarda | A61B 18/1492 600/374 |
| 2004/0133113 | A1* | 7/2004 | Krishnan | A61B 5/042 600/508 |
| 2006/0195081 | A1* | 8/2006 | Landis | A61B 17/2812 606/41 |
| 2010/0030298 | A1* | 2/2010 | Martens | A61N 1/0529 607/45 |
| 2014/0257261 | A1* | 9/2014 | Kim | A61B 5/0422 606/21 |

* cited by examiner

*Primary Examiner* — Eun Hwa Kim
(74) *Attorney, Agent, or Firm* — Abelman, Frayne & Schwab

(57) ABSTRACT

The invention relates to a catheter useful in recording His electrogram alternans. The catheter includes a catheter probe containing at least one row of receiving poles positioned at an edge of the catheter probe, equidistantly spaced from each other.

8 Claims, 3 Drawing Sheets

Fig 1 PRIOR ART
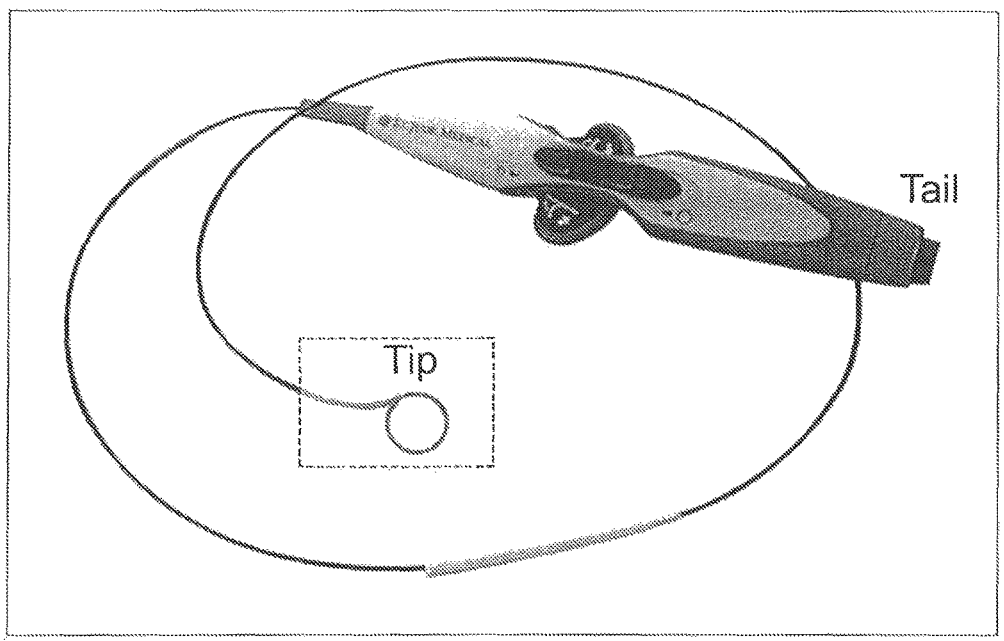
Fig 2a PRIOR ART
Fig 2b PRIOR ART
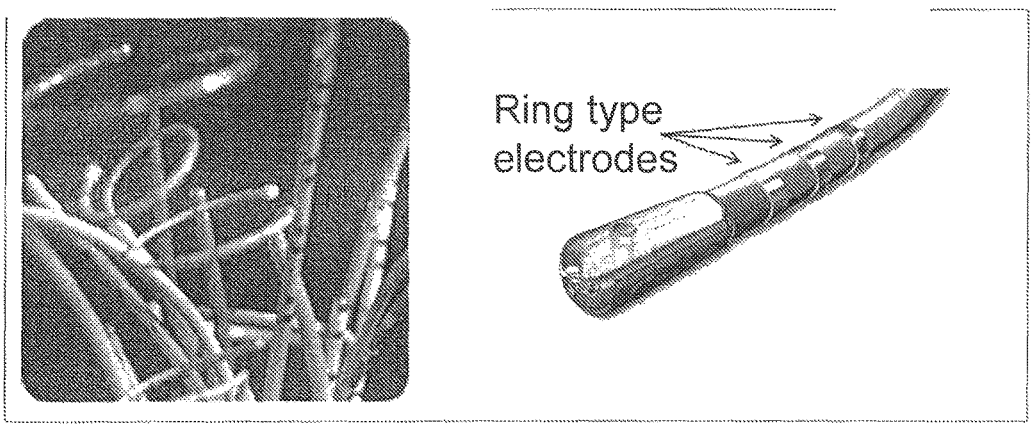

Figure 3
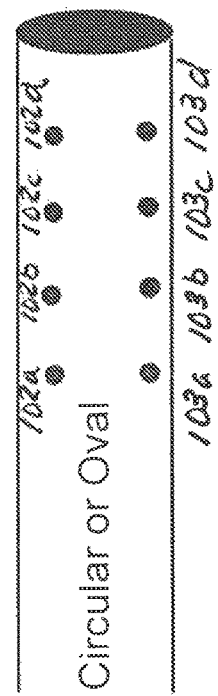
Fig 3A
Circular or Oval
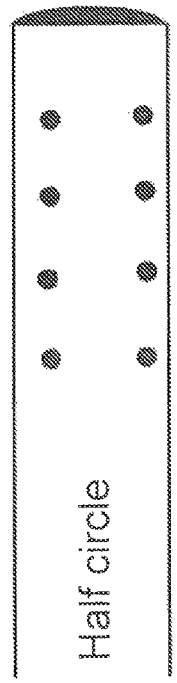
Fig 3B
Half circle
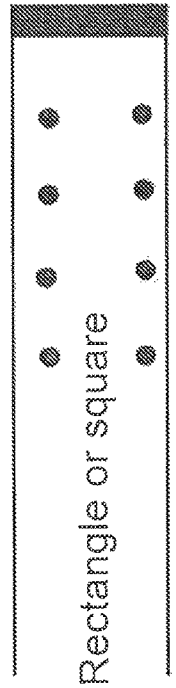
Fig 3C
Rectangle or square
Fig 3D
The electrodes can be circular, oval or other types

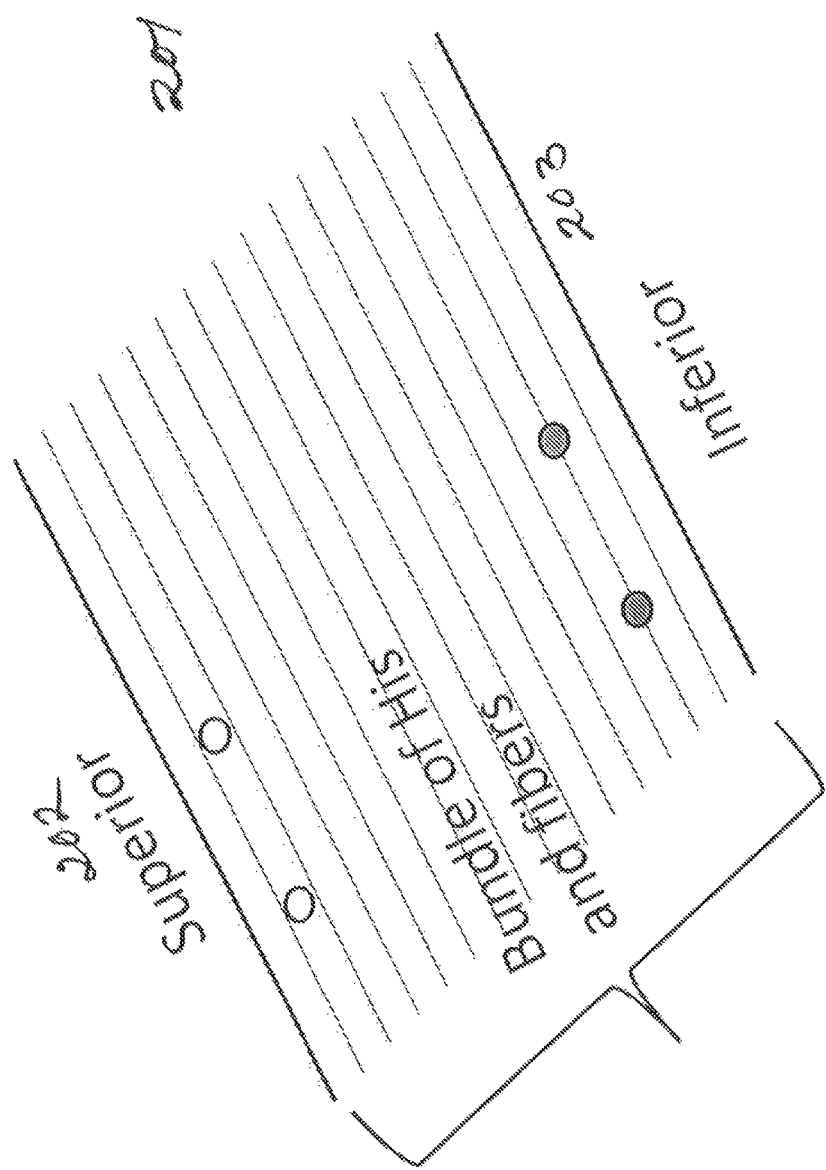

CATHETER FOR USE IN RECORDING HIS ELECTROGRAM ALTERNANS AND APPLICATION TO VARIOUS CONDITIONS

RELATED APPLICATION

This application claims priority from U.S. Provisional Application No. 62/056,902 filed Sep. 29, 2014, incorporated by reference in its entirety.

FIELD OF THE INVENTION

The invention relates to an apparatus useful in determining an electric signal from cardiac tissue. More specifically, it relates to a catheter probe useful in determining electrical signals from the cardiac tissue referred to as the His bundle, or "bundle of His".

BACKGROUND AND PRIOR ART

In 2001, Zhang et al., *Circulation*, 104:832-838 (2001), the disclosure of which is incorporated by reference, described a phenomenon termed "His electrogram alternans," or "HE alternans." It was observed that by recording HE alternans, the clinician may visualize atrioventricular (AV) nodal dual pathway conduction. In addition to Zhang, supra, see Zhang, et al., *Circulation*, 107:1059-1065 (2003); Zhang, et al. *Cardiovascular Research*, 61:45-55 (2004); Zhan, et al., *J. Cardiovasc. Electrophys.*, 22:1256-1262 (2011); Zhang, et al., *Int. J. Cardiology*, 171:259-264 (2014); and Zhang, et al., *J. Interv. Card. Electrophysiol.*, 40:99-103 (2014); all of which are incorporated by reference.

The concept of dual pathway AV node electrophysiology was developed, initially, to explain AV nodal re-entrant tachycardia (AVNRT), which is the most common type of paroxysmal supraventricular tachycardia. Prior to the observation described supra, also called Zhang's Phenomenon, there were no tools or values available which could be used to monitor dual pathway conduction with the exception of a "sudden jump" in the AV node conduction curve. This "sudden jump" was defined as a sudden increase of AV conduction time, of 50 mseconds (ms) or more with premature beats shortened in 10 ms steps. While it was believed that this sudden jump resulted from a switch of AV conduction from fast to slow pathway conduction, not every patient was, or is, seen to exhibit this jump. An additional issue is that this jump is only revealed when the whole AV conduction curve is studied. No methodologies were available, before the discovery of Zhang's phenomenon, to monitor dual pathway AVN conduction on a beat-by-beat basis. Prior to the invention, dedicated means for determining it were not available. It is now believed that dual pathway AV node conduction may exist in all patients, and determining HE alternans can be used in routine clinical cardiac electrophysiology in order to monitor dual pathway AV conduction. The phenomenon is especially useful during catheter ablation of atrioventricular nodal reentrant tachycardia, or any AV node modification approach involving dual pathway AVN conduction, including AVN modification to slow ventricular rates during atrial fibrillation.

At present, His electrogram recording is done, routinely, during clinical cardiac electrophysiology examination. It is only used as a marker of electrical excitation reaching the His bundle. In other words, it is used to measure AV conduction time intervals, and His ventricular intervals. It is not used as an index of dual pathway AV nodal conduction.

It is a purpose of this invention to facilitate the measurement of this phenomenon by way of an easily manufactured, easily used device.

The medical arts are replete with various catheter probes which are used either to receive information from tissue, such as cardiac tissue, or to deliver signals, such as electrical charges. An exemplary, but by no means exhaustive list of references showing various embodiments of catheters includes EP 499 491; U.S. Pat. No. 4,649,924; PCT/US94/03768; U.S. Pat. Nos. 4,974,588; 5,063,932; 5,184,620; 8,777,851; Published U.S. Patent Application 2014/0128935, and Published U.S. Patent Application 2012/0108993.

Even a cursory review of this sampling of the literature will show that for catheters "form follows function." In other words, the shape of the catheter, including the catheter tip or probe, and the extended member which leads to the tip or probe, will change, depending upon the intended function of the catheter. Similarly, while all of these catheters incorporate electric poles, some, such as pace maker type devices are designed to discharge an electrical signal, while others include poles which receive and transmit an electrical signal.

Typically, electrophysiology catheters have essentially the same form, with a body, "tail," and "tip," as is shown in FIG. 1. To the extent that these "EP" catheters differ, they differ in the tip. FIG. 2a shows various types of prior art tips, and FIG. 2b, "ring type" electrodes, which are common.

In order to carry out functions as described herein, a catheter must be designed such that it can be placed in a blood vessel, e.g., a vein or an artery, which leads to cardiac tissue, such as cardiac muscle, the His bundle in particular. Further, the catheter tip or probe must be designed to fit precisely on the targeted cardiac tissue, i.e., the His bundle.

As will be shown in the disclosure which follows, the inventor has developed a catheter means which fulfills the requirements discussed supra. The details thereof will be elaborated upon in the disclosure which follows.

BRIEF DESCRIPTION OF THE FIGURES

FIG. 1 labeled PRIOR ART shows a commercially available electrophysiology catheter.

FIG. 2a labeled PRIOR ART shows various types of electrophysiology catheter tips.

FIG. 2b labeled PRIOR ART shows typical ring type electrodes as used in the field.

FIGS. 3a-3d show different embodiments of the invention.

FIG. 4 shows a schematic view of the His bundle its fibers, and preferred placement of electrode pole onto the superior (open circles) and inferior (closed circles) bundle.

DETAILED DESCRIPTION OF THE PREFERRED EMBODIMENTS

Referring now to the drawings, one example of a preferred embodiment of the invention is shown, in FIG. 3. In FIG. 3, one sees different configurations a, b, c, and d, of the tip of a catheter in accordance with the invention. The different configurations of the tip of the catheter are shown, so as to depict geometries which are useful in determining HE alternans. The tip of the catheter must be configured so as to rest stably on the cardiac structure known as the His bundle. Shown in FIGS. 3a-3c, respectively, are circular oval, and rectangular (square) configurations. These embodiments are all bilaterally symmetrical. The configurations can also be other shapes, such as semi-circles, squares, or rectangles.

Configurations shown in FIGS. 3A, 3B, and 3C all show two rows of parallel, receiving electric poles. These are shown by 102a, b, c, and d and 103a, b, c, and d in FIG. 3A, and these indicia apply for each figure. The poles are positioned at the end of the catheter, and the distance between any two poles in a horizontal row is the same for all others in that row. Similarly, the vertical distance between two corresponding poles is the same for all corresponding poles. Finally, the distance between terminal pole and the end of the catheter is always the same in a given catheter.

As the His bundle is a relatively small structure, the electric receiving poles are small, preferably from about 1 mm to 2 mm in diameter. Spacing of the electric receiving poles in a row from each other is about 2-4 mm.

The catheter tip of the invention may vary in size, however, as it must be inserted through a peripheral blood vessel into the chamber of the heart where the His bundle is located, preferably the tip is from about 3-5 mm wide (or, from about 3-5 mm in diameter if a circular or semicircular configuration is used). The tip is from about 6 to about 10 cm in length, and may present receiving poles along its full length, or part of its length. If the poles are only presented along a position of the length, it is preferred that they be at the distal end of the tip, relative to the catheter lead. Poles should be presented as close to the edges of the tip as possible. The poles can be configured in the shapes discussed supra.

The materials used to make the catheter tip are the standard materials used to make catheters, and these will be readily familiar to those of ordinary skill in the art. Exemplary materials for the body of the tip are polyurethanes, with platinum, iridium, or alloys thereof being used to manufacture the receiving poles. Other materials will be known to the skilled artisan and need not be provided here.

Each row should contain the same number of electric receiving poles, when the catheter employs two rows. Each row must contain at least two poles, but preferably contains at least 4-8.

In a further embodiment of the invention, depicted in FIG. 3d, the catheter only records one of the two HE values (SHE or IHE, i.e., superior or inferior His electrogram alternans). In this embodiment, the requirements of parallel rows are not present; however, the other dimensionalities apply here as well.

In operation, the catheter of the invention functions in a manner set forth in FIG. 4. FIG. 4 shows a rough schematic of the His bundle, 201. It can be seen that the His bundle has superior inferior positions 202 and 203. In operation, the end of the catheters shown in FIG. 3 are configured to fit precisely on top of the His bundle, such that the receiving poles record both the superior His electrogram value, and the inferior His electrogram value. The catheter end depicted in 3d is used to record one or the other of these values. Fitting of the catheter tip onto the His bundle can be accomplished via, for example, using an external control mechanism to curve the tip to the degree necessary.

The skilled artisan will recognize that this catheter tip or probe is integrally connected to a flexible, elongate member, which is suitably small so as to pass easily through a blood vessel, e.g., a vein leading to a heart.

Other embodiments of the invention will be clear to the skilled artisan and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

I claim:

1. A method for determining His electrogram alternans (HEA) from a His bundle of cardiac tissue, said His bundle comprising a superior His domain and an inferior His domain comprising inserting an apparatus for receiving electrical signals from an His bundle of cardiac tissue through a human blood vessel, said apparatus comprising a catheter tip portion at one end and a flexible elongate member at the other end, wherein said catheter tip portion comprises a first and a second row of parallel, receiving electric poles positioned at a first and a second edge on a flat surface of said catheter tip portion, wherein any two of said parallel receiving electric poles in a horizontal row are separated from each other at a distance equal to the distance between any other pair of corresponding receiving electric poles in a horizontal row, wherein said catheter probe is from about 6 cm to about 10 cm in length, and from about 3 mm to about 5 mm in width or diameter, said catheter tip portion being in the form of a bilaterally symmetrical rectangle, semi-circle, or square, and positioning said catheter tip portion on said His bundle of cardiac tissue, so that the first row of receiving electric poles align along said superior His domain and said second row of receiving electric poles align along said inferior His domain, to determine said HEA.

2. The method of claim 1, wherein said HEA comprises a SHE (superior His electrogram) and an IHE (inferior His electrogram).

3. The method of claim 1, wherein said blood vessel is a vein.

4. The method of claim 1, wherein said blood vessel is an artery.

5. A method for determining His electrogram alternans (HEA) from a His bundle comprising a superior His domain and an inferior His domain of cardiac tissue, comprising inserting an apparatus for receiving an electrical signal from an His bundle of cardiac tissue through a human blood vessel, said apparatus comprising a catheter tip portion at one end and a flexible elongate member at the other end, wherein said catheter tip portion comprises a first and a second row of parallel, receiving electric poles positioned at a first and a second edge on a surface of said catheter tip portion, wherein any two of said parallel receiving electric poles in a horizontal row are separated from each other at a distance equal to the distance between any other pair of corresponding receiving electric poles in a horizontal row, wherein said catheter probe is from about 6 cm to about 10 cm in length, and from about 3 mm to about 5 mm in width or diameter, said catheter tip portion being in the form of a bilaterally symmetrical oval and positioning said catheter tip portion on said His bundle of cardiac tissue, so that the first row of receiving electric poles are aligned along the superior His domain and the second row of receiving electric poles align along the inferior His domain, to determine said HEA.

6. The method of claim 5, wherein said electric HEA comprises a SHE (superior His electrogram) and an IHE (inferior His electrogram).

7. The method of claim 5, wherein said blood vessel is a vein.

8. The method of claim 5, wherein said blood vessel is an artery.

\* \* \* \* \*